US010213292B2

(12) United States Patent
Arai et al.

(10) Patent No.: US 10,213,292 B2
(45) Date of Patent: Feb. 26, 2019

(54) HYBRID ANCHOR

(71) Applicant: Smith & Nephew, Inc., Memphis, TN (US)

(72) Inventors: Tatsuya Arai, Houston, TX (US); Matthew Koski, Westford, MA (US)

(73) Assignee: Smith & Nephew, Inc., Memphis, TN (US)

(*) Notice: Subject to any disclaimer, the term of this patent is extended or adjusted under 35 U.S.C. 154(b) by 326 days.

(21) Appl. No.: 14/403,905

(22) PCT Filed: May 29, 2013

(86) PCT No.: PCT/US2013/043047
§ 371 (c)(1),
(2) Date: Nov. 25, 2014

(87) PCT Pub. No.: WO2013/181212
PCT Pub. Date: Dec. 5, 2013

(65) Prior Publication Data
US 2015/0142024 A1    May 21, 2015

Related U.S. Application Data

(60) Provisional application No. 61/652,520, filed on May 29, 2012.

(51) Int. Cl.
A61F 2/08      (2006.01)
A61B 17/04    (2006.01)
A61B 17/00    (2006.01)

(52) U.S. Cl.
CPC ......... *A61F 2/0811* (2013.01); *A61B 17/0401* (2013.01); *A61B 2017/00831* (2013.01);
(Continued)

(58) Field of Classification Search
CPC ............ A61F 2/0811; A61F 2002/0888; A61F 2002/0841; A61F 2002/0829;
(Continued)

(56) References Cited

U.S. PATENT DOCUMENTS 5,480,403 A    1/1996  Lee et al.
RE36,289 E    8/1999  Le Thu et al.
(Continued)

FOREIGN PATENT DOCUMENTS

WO    9516399 A1    6/1995

OTHER PUBLICATIONS

PCT International Search Report and Written Opinion of the International Searching Authority corresponding to PCT/PCT/US2013/043047, dated Aug. 20, 2013; 3 pages.
(Continued)

*Primary Examiner* — Anh T Dang
(74) *Attorney, Agent, or Firm* — Burns & Levinson, LLP; Joseph M. Maraia

(57) ABSTRACT

Some materials used to make anchors for soft tissue repair, for example, have beneficial properties, including stiffness, bioabsorbability, and osteoconductivity. These materials, however, are not flexible and are challenging to make flexible wings out of for winged anchors. Wing flex is desirable for achieving high fixation strength in winged anchors. Accordingly, an anchor is provided having a hybrid structure including a core body made from a biocomposite, bioabsorbability, osteoconductivity or biocompatible non absorbable material and a wing assembly made from different and more flexible material. Examples of the hybrid anchor take advantage of properties of the different materials strategically placed. A no-hole-prep example of the hybrid anchor reduces the time to install the anchor. A modular example of the hybrid anchor provides a customizable anchoring solution to meet a variety of diverse clinical needs.

19 Claims, 7 Drawing Sheets

(52) U.S. Cl.
CPC ............... *A61B 2017/00964* (2013.01); *A61B 2017/0414* (2013.01); *A61B 2017/0435* (2013.01); *A61B 2017/0437* (2013.01); *A61F 2002/0829* (2013.01); *A61F 2002/0841* (2013.01); *A61F 2002/0858* (2013.01); *A61F 2002/0888* (2013.01); *A61F 2250/0018* (2013.01)

(58) Field of Classification Search
CPC .... A61B 2017/0435; A61B 2017/0437; A61B 2017/00964; A61B 17/0401
See application file for complete search history.

(56) References Cited

U.S. PATENT DOCUMENTS

| | | | |
|---|---|---|---|
| 2006/0106422 A1 | 5/2006 | Del Rio et al. | |
| 2011/0112576 A1* | 5/2011 | Nguyen | A61B 17/0401 606/232 |
| 2012/0059384 A1* | 3/2012 | Fan | A61F 2/0805 606/104 |

OTHER PUBLICATIONS

Patent Examination Report from related Australian Application No. 2013267565 dated Nov. 4, 2016.

* cited by examiner

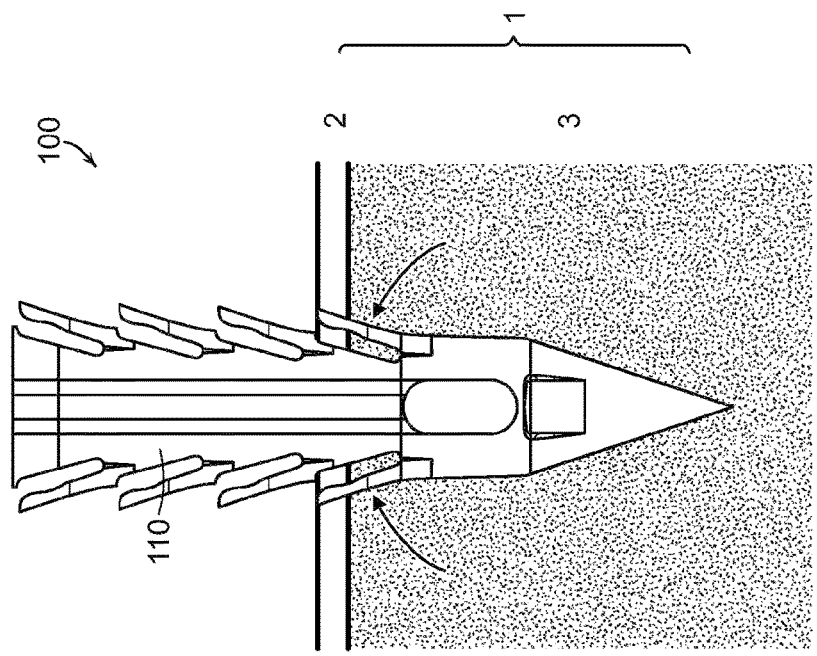
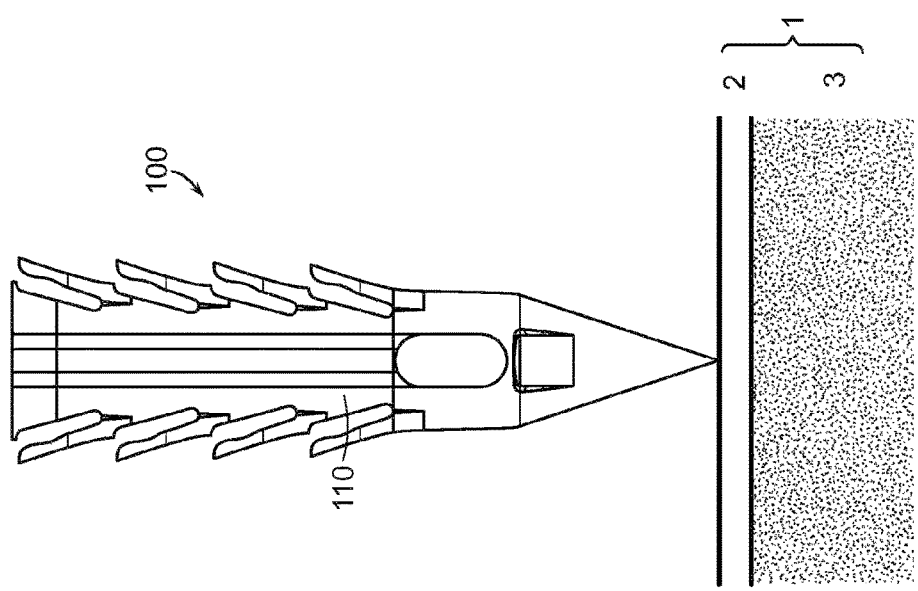

HYBRID ANCHOR

CROSS REFERENCE TO RELATED APPLICATIONS

This application is a U.S. national stage application under 35 U.S.C. 371 of co-pending International Application No. PCT/US2013/043047 filed on May 29, 2013 entitled HYBRID ANCHOR. International Application No. PCT/US2013/043047 claims priority to U.S. Provisional Patent Application No. 61/652,520 filed on May 29, 2012. All of the above-referenced applications are incorporated by reference herein in their entirety for all purposes.

BACKGROUND

Whether because of disease or injury, soft tissue may become detached from bone. A surgeon can use a variety of anchors to reattach soft tissue to bone. Generally, one or more anchors are inserted into bone and the detached tissue is reattached to the bone either by the anchor itself or by one or more sutures coupled to the anchor. Great demands are placed on the anchor. When inserting the anchor into bone, the anchor must have structural strength (e.g., axial and/or torsional strength) to withstand the force/stress of inserting the anchor into the bone. This is especially true when the anchor is inserted into bone without a hole drilled into the bone, a so called "no-hole-prep" approach. Once installed, the anchor must have high fixation strength to resist being pulled out, for example, by the surgeon tensioning the suture.

One anchor design uses wings, which project outwardly, for securing the anchor into bone. Flexibility of the wings is important to achieving high fixation strength. When the anchor is inserted, the wings fold inwardly or comply with the hard outer cortical layer of the bone. Once the anchor is inserted, the wings hold outwardly to flexibly capture to the soft inner cancellous layer of the bone. Making a winged-anchor out of one biocompatible material that is both structurally strong and flexible is challenging. Current state-of-the-art biocompatible materials that are structurally strong, such as carbon fiber reinforced polyether ether ketone (CF PEEK) are stiff and lack sufficient flexibility for achieving high fixation strength in a winged-anchor.

SUMMARY

Described herein are examples of an anchor of a hybrid design that address the foregoing shortcomings and others as well. A hybrid anchor includes a core body and a sleeve with wings. The core body is made of a material selected from the group consisting biocompatible, bioabsorbable, osteoconductive, biocomposite and combinations thereof. The sleeve is made of a polymer. The polymer making up the sleeve is different and more flexible than the material of the core body The core body has a proximal end, distal end, and longitudinal axis extending therethrough. The core body includes a force receiving member disposed at the proximal end of the core body. The force receiving member configured to engage an inserter and to receive an insertion force applied by the inserter to the core body. The core body further includes a tip disposed at the distal end of the core body. The core body further includes an elongated member extending between the force receiving member and tip along the longitudinal axis of the core body.

The sleeve has a proximal end, distal end, and surface extending therebetween. The sleeve includes a plurality of wings formed on diametrically opposing sides of the sleeve and extending outwardly from the surface of the sleeve at an angle towards the proximal end of sleeve. The sleeve fitted around the elongated member of the core body and captured between the tip and force receiving member of the core body.

Further areas of applicability of the present disclosure will become apparent from the detailed description provided hereinafter. It should be understood that the detailed description and specific examples, while indicating the convenient example of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate examples of the present disclosure and together with the written description serve to explain the principles, characteristics, and features of the disclosure. In the drawings:

FIGS. 2A-C are side views of the example hybrid anchor being inserted into bone.

DETAILED DESCRIPTION

The following description of examples is in no way intended to limit the disclosure, its application, or uses.

Figure 1:
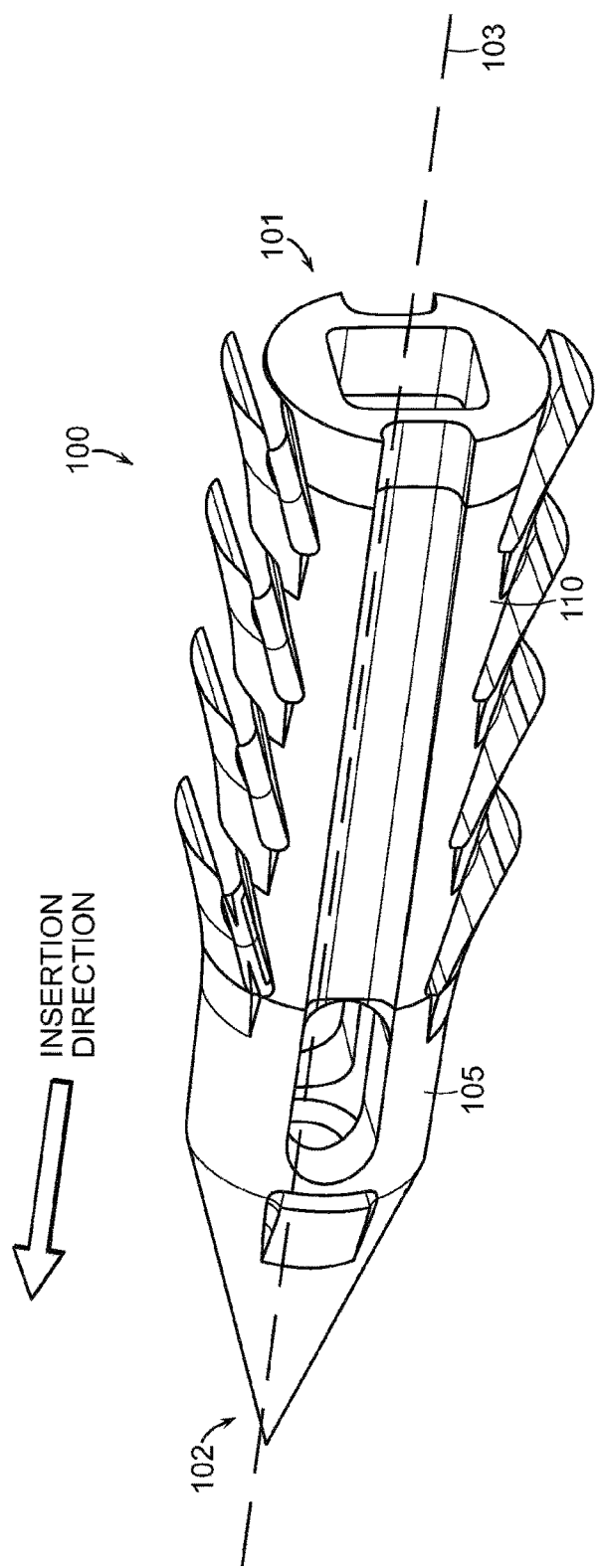
FIG. 1 is an isometric view of an example of a hybrid anchor.

FIG. 1 shows an example of a hybrid anchor 100 having a proximal end 101, distal end 102, and longitudinal axis 103 extending between the ends. A surgeon applies an insertion force to the proximal end 101 (e.g., with an inserter) to first insert the distal end 102 into bone, and then to insert the remaining portion of the hybrid anchor 100. The hybrid anchor 100 includes a core body 105 and wing assembly 110. The hybrid anchor 100 is a winged anchor relying on flexible wings to hold or "fix" the hybrid anchor 100 into bone once inserted.

The core body 105 is made from a biocomposite material, such as CF PEEK. The biocomposite core body 105 is stiff along the longitudinal axis 103 of the hybrid anchor 100, which is generally aligned with the direction that the hybrid anchor 100 is inserted or "insertion direction." Owing, in part, to its stiffness in the insertion direction, the biocomposite core body 105, is particularly well-suited for no-hole-prep insertion into bone (i.e., without a hole drilled into bone). The biocomposite core body 105 further includes a tip configured for no-hole-prep installation into bone. The tip and other elements of the hybrid anchor 100 are described in greater detail below.

Another example of the hybrid anchor 100 includes a core body made from a bioabsorbable polymer, e.g., polylactic acid (PLA), polyglycolic acid (PGA). The bioabsorbable core body is absorbed by a patient's body over time. This absorption is advantageous because new bone tissue growth replaces the bioabsorbable core body 105 and reduces the amount of foreign material that remains in the patient's body.

Still another example of the hybrid anchor 100 includes a core body made from osteoconductive material, such as polymorphous low-grade adenocarcinoma (PLGA) with calcium-based filler. The osteoconductive core body provides a "bone scaffold" onto which grow new bone. The osteoconductive core body is particular advantageous in applications where generating and maintaining bone is desirable.

Still yet another example of the hybrid anchor 100 includes a core body made from a biocompatible, non-absorbable material, such as surgical grade stainless steel and titanium. The biocompatible, non-absorbable core body has a material strength that is generally higher than biocompatible, absorbable material. As such, the biocompatible, non-absorbable core body is well suited for clinical applications requiring higher material strength.

The foregoing materials generally provide the substantial structure strength needed to advance the hybrid anchor 100 into bone (and in some instance, without a hole drilled into the bone). As such, these materials are well suited for the core body 105 of the hybrid anchor 100. Some of the foregoing materials, however, are not flexible enough to be wings of a winged anchor. Others are difficult and/or costly to make into wings.

Figure 2C:
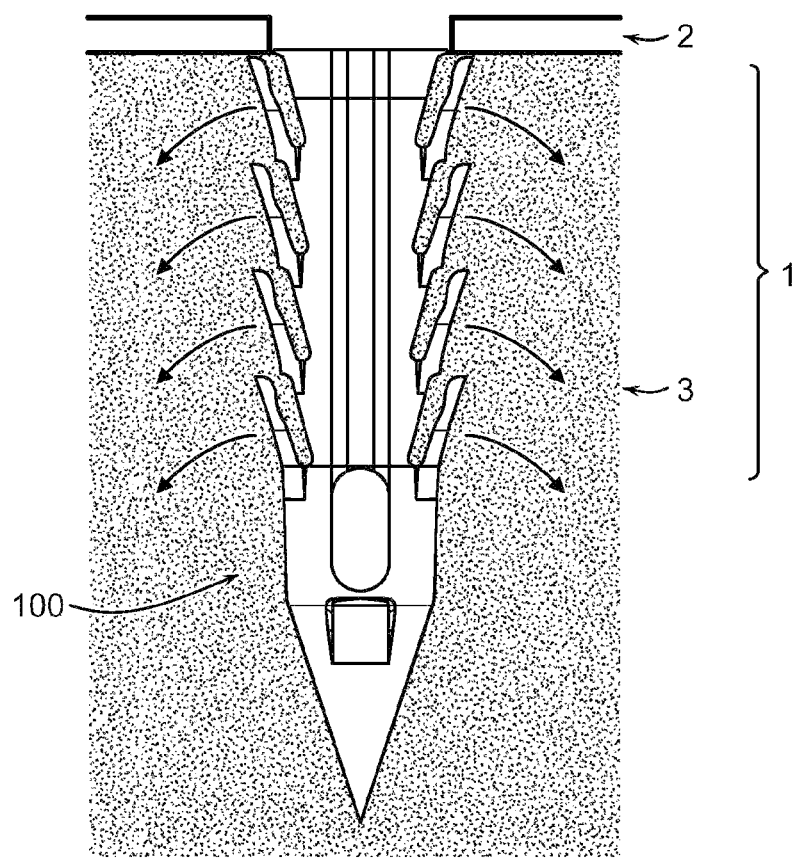

In the hybrid anchor 100, the wing assembly 110 is made from a material different from the material of the core body 105. Additionally, the material of the wing assembly 110 is more flexible than the material of the core body 105. In a convenient example of the hybrid anchor 100, the wing assembly 110 is made from polyether ether ketone (PEEK). Other examples include acrylonitrile butadiene styrene (ABS). With reference to FIGS. 2A-2C, as the hybrid anchor 100 is inserted into bone 1, the wings of wing assembly 110 fold inwardly to comply with the hard outer cortical layer 2 of the bone 1. Once the hybrid anchor 100 is inserted into the bone 1, the wings of wing assembly 110 fold outwardly to flexibly capture the soft inner cancellous layer 3 of the bone 1.

The hybrid structure of the core body 105 and wing assembly 110 takes advantage of different materials strategically placed in the hybrid anchor 100. Part of the hybrid anchor 100 has the property of stiffness, bioabsorbability or osteoconductivity, while another part has the property of flexibility. Advantageously, examples of the hybrid anchor 100 include, a biocomposite winged anchor, bioabsorbable winged anchor, and osteoconductive winged anchor, each with high fixation strength.

Figure 3:
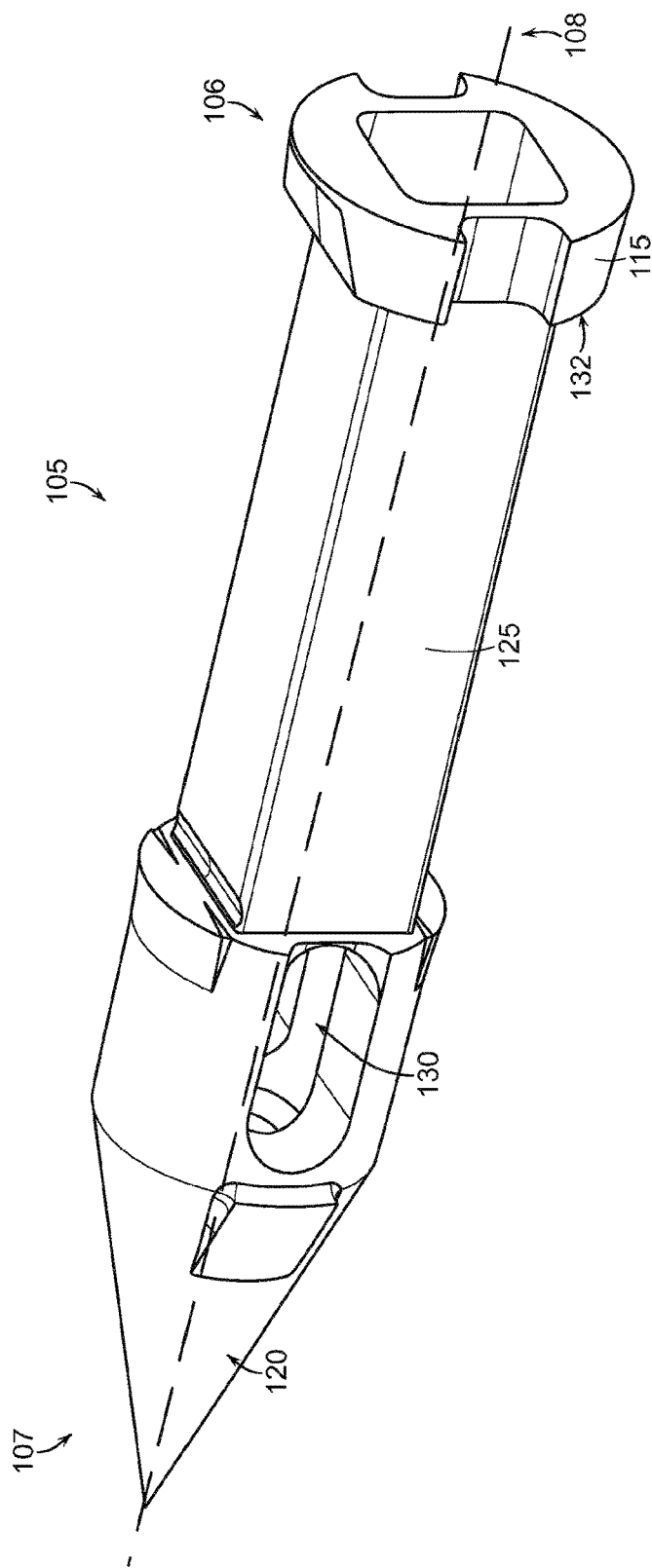
FIG. 3 is a view of a core body of the example hybrid anchor.

FIG. 3 shows an example of the core body 105 having a proximal end 106, distal end 107, and longitudinal axis 108 extending between the ends. The core body 105 includes, at the proximal end 106, a force receiving member 115 and, at the distal end 107, a tip 120. The core body 105 further includes an elongated member 125 extending between the force receiving member 115 and tip 120 and along the longitudinal axis 108 of the core body 105.

Together the force receiving member 115, tip 120, and elongated member 125 from a continuous path through which a substantial portion of the insertion force travels from the proximal end 106 to distal end 107 of the hybrid anchor 100. Advantageously, this arrangement of the core body 105 delivers an impulsive force applied to the proximal force receiving member 115 from an inserter to the distal tip 120. This arrangement of the core body 105 also supports a torque applied by the inserter to lift up soft tissue to, for example, acquire a proper angle to insert the hybrid anchor 100 into bone.

The elongated member 125 provides a means for coupling the core body 105 and wing assembly 110, radially. Because of the radial coupling the wing assembly 110 does not directly receive an axial insertion force from an inserter (e.g., impact/impulse force from a mallet). Instead, the wing assembly 110 undergoes friction (resistive force) and radial stress from bone that is substantially less than the axial insertion force. Even in the event of the core body 105 and wing assembly 110 separating, the wing assembly 110 still undergoes friction and radial stress. Advantageously, the radial coupling between core body 105 and wing assembly 110 protects the hybrid anchor 100 from damage and inhibits hybrid anchor 100 from failing.

The elongated member 125 and wing assembly 110 are made of different materials with different flexibility (or stiffness). As such, the elongated member 125 and wing assembly 110 form an interface. Examples of the interface between the core body 105 and wing assembly 110 include but not limited to friction, which may be selected based on the surface roughness of the elongated member 125, interference fit and overmolding the wing assembly 110 onto the elongated member 125. As shown, the example elongated member 125 has a cross-section that is substantially a square. Other cross-sections are possible, including a circular cross-section, oval cross-section, regular polygonal cross-section, and irregular polygonal cross-section.

The force receiving member 115 receives an insertion force delivered by an inserter, such as a driver or mallet. In some situations, the insertion force is delivered substantially aligned with the longitudinal axis 108 of the core body 105 (and from the longitudinal axis 103 of the hybrid anchor 100). In other situations, the insertion force is delivered "off axis," e.g., 5° to 10° from the longitudinal axis 108 of the core body 105 (and from the longitudinal axis 103 of the hybrid anchor 100).

Some examples of the force receiving member 115 include retaining features otherwise couple the hybrid anchor 100 to the inserter. Such features include but not limited to pin-slot and ball detent locking mechanisms. When the hybrid anchor 100 is for no-hole-prep and the inserter is a mallet, the force receiving member 115 includes a pounding surface. The surface may be substantially flat, crowned or have shape suitable for receiving blows from the mallet.

The core body 105 further includes a stop 132. The stop 132 resists the urge of the wing assembly 110 to translate in a direction opposite the insertion direction. As the wing assembly 110 enters bone and experiences a resistive force (e.g., friction from the bone), the wing assembly 110 tends to move towards the proximal end 106 of the core body 105 (and of the hybrid anchor 100) in response. In some situations, the resistive force is sufficiently high causing a "backward" motion of the wing assembly 110 that shears the wing assembly 110 off of the elongated member 125. The stop 132 inhibits this mode of failure of the hybrid anchor 100. As shown, the stop 132 is defined by one end of the force receiving member 115. In other examples, the stop 132 is formed by the elongated member 125. In still other examples, the stop 132 is a separate component of the core body 105.

The tip 120 is configured to be inserted into bone. As shown, the tip 120 has a point suitable for penetrating the hard outer cortical layer of bone without a hole drilled into the bone. This tip 120 geometry is particularly advantageous because it eliminates the step of drilling a hole. Consequently, a surgeon can insert a no-hole-prep hybrid anchor in less time than, for example, a conventional screw-in anchor. The surgeon can also install more no-hole-prep hybrid anchors in a given period of time. As such, some examples of the hybrid anchor 100 can shorten surgery time.

Other examples of the tip 120 have geometries suited for installing in a hole drilled into bone, called a "bone hole." The geometries include a truncated cone, which is easier to install into a bone hole, particularly one that is undersized. These tip 120 examples are advantageously combined with core bodies made of bioabsorbable or osteoconductive material. Generally, bioabsorbable and osteoconductive materials are too brittle for no-hole-prep and require a bone hole for insertion.

Other examples of the core body 105 further include an aperture 130 configured to receive one or more sutures. The shape and size of the aperture 130 is selected based, at least in part, on the size of a suture, the number of sutures, and the shape of a suture to be received in the aperture 130. For example, the aperture 130 is shown having elongated form. This elongated aperture 130 is particularly well suited for receiving the flat profile of suture tape or several round sutures.

As shown in the figure, the aperture 130 is transverse to the longitudinal axis 108 of the core body 105. The aperture 130 is formed near the distal end 107 of the core body 105. In other examples of the core body 105, the aperture 130 is formed at distal end 107 of the core body 105. One example of the core body 105 includes a substantially a U-shaped aperture. The opened end of the U-shaped aperture defines the distal most end 102 of the hybrid anchor 100. A surgeon captures a suture (e.g., to bring the suture to bone hole) by simply straddling the suture with the opened end of the U-shaped aperture. This open-ended construct is advantageous because it takes less time than threading the suture through a closed eyelet.

Figure 4:
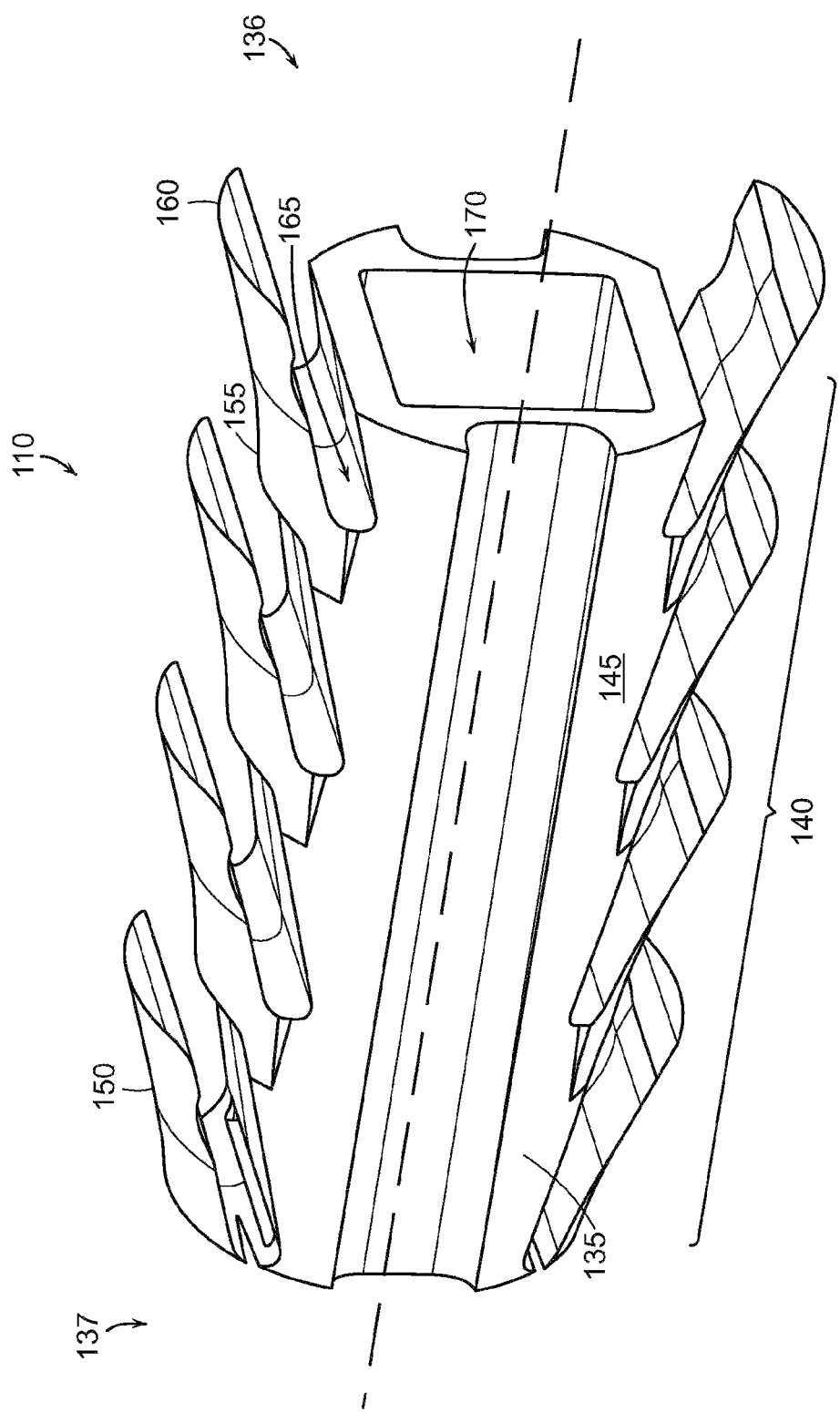
FIG. 4 is view of a wing assembly of the example hybrid anchor.

FIG. 4 shows the wing assembly 110 having a sleeve 135 and a plurality of wings 140. The sleeve 135 has a proximal end 136, distal end 137, and a surface 145 extending between the ends. The plurality of wings 140 is formed on the surface 145 of the sleeve 135. As shown, the plurality wings are grouped into two rows, each diametrically opposed to one another. In a convenient example, the plurality of wings 140 is formed on diametrically opposing sides of the sleeve 135. Other examples of the wing assembly 110 include more than 2 two rows of wings (e.g., 3 or 4 rows) radially arranged about the sleeve 135.

Turning now to an individual wing 150. In more detail, the wing 150 includes a base 155 and a wing tip 160. The wing 150 extends outwardly from the base 155, at an angle to the surface 145 of the sleeve 135, towards the proximal end 136 of the sleeve 135. The angle is selected so that the wing 150 flexes inwardly with the wing tip 160 moving towards the surface 145 of the sleeve 135 in response to an insertion force. The wings flexes outwardly with the wing tip 160 moving away from the surface 145 of the sleeve 135 in response to a pull out force.

The wing 150 further includes, at the base 155, a clearance 165. The dimensions of the clearance 165 (e.g., length, width, and radius) are selected to provide the wing 150 with suitable flexibility. The wings further have a profile defined between the base 155 and wing tip 160. The profile is selected to provide sufficient resistance to being pulled out. For example, as shown, the profile of the wing 150 flares outwardly near the wing tip 160. This flared profile is designed to catch the hard outer cortical layer when the wing assembly 110 is withdrawn from bone. Accordingly, such a profile is advantageous to achieving high fixation strength of the hybrid anchor 100.

The sleeve 135 includes longitudinal bore 170 extending the entire length of the sleeve 135. The longitudinal bore 170 has a shape corresponding to the cross-section of the elongated member 125. As shown, the longitudinal bore 170 is substantially square in shape corresponding to square cross-section of the elongated member 125. Other examples of the longitudinal bore 170 have shapes that are the inverse of a circular cross-section, oval cross-section, regular polygonal cross-section, and irregular polygonal cross-section.

Figure 5A:
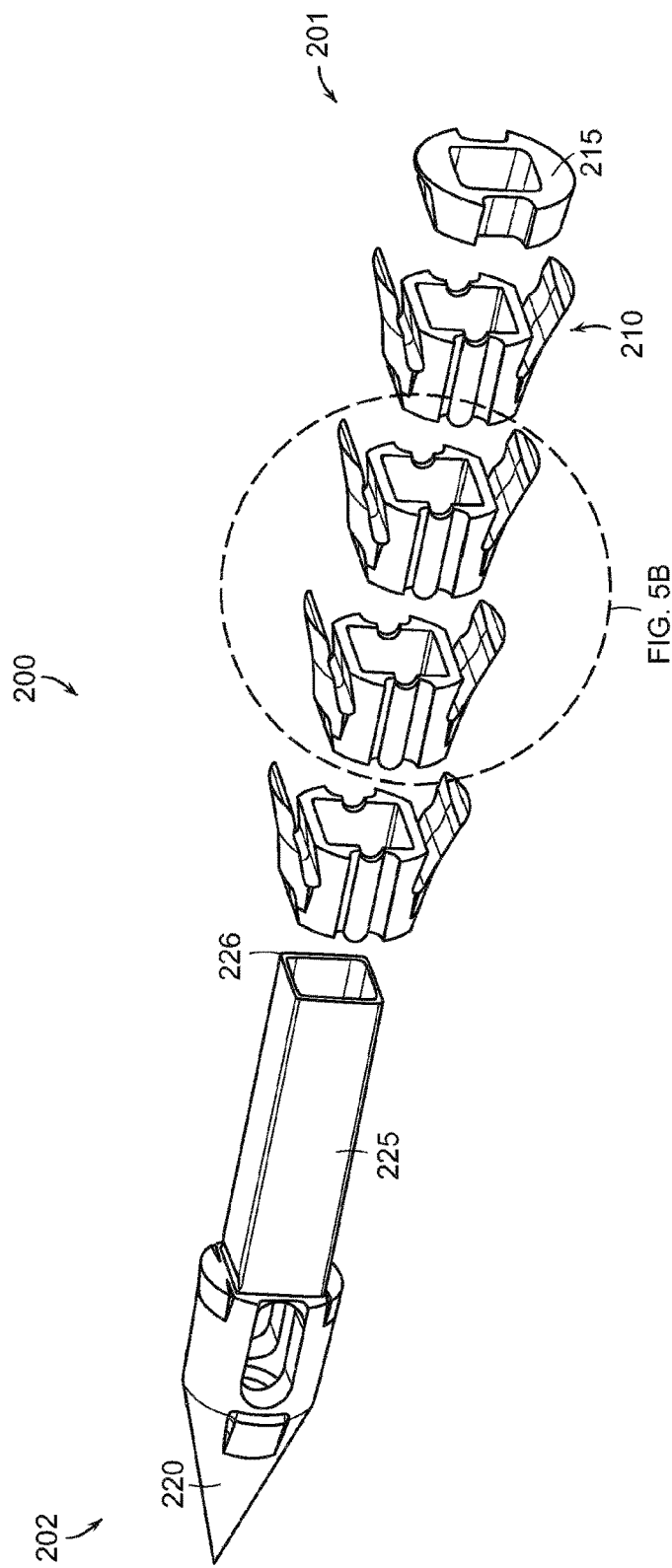
FIGS. 5A and 5B are views modular example of the hybrid anchor.
Figure 5B:
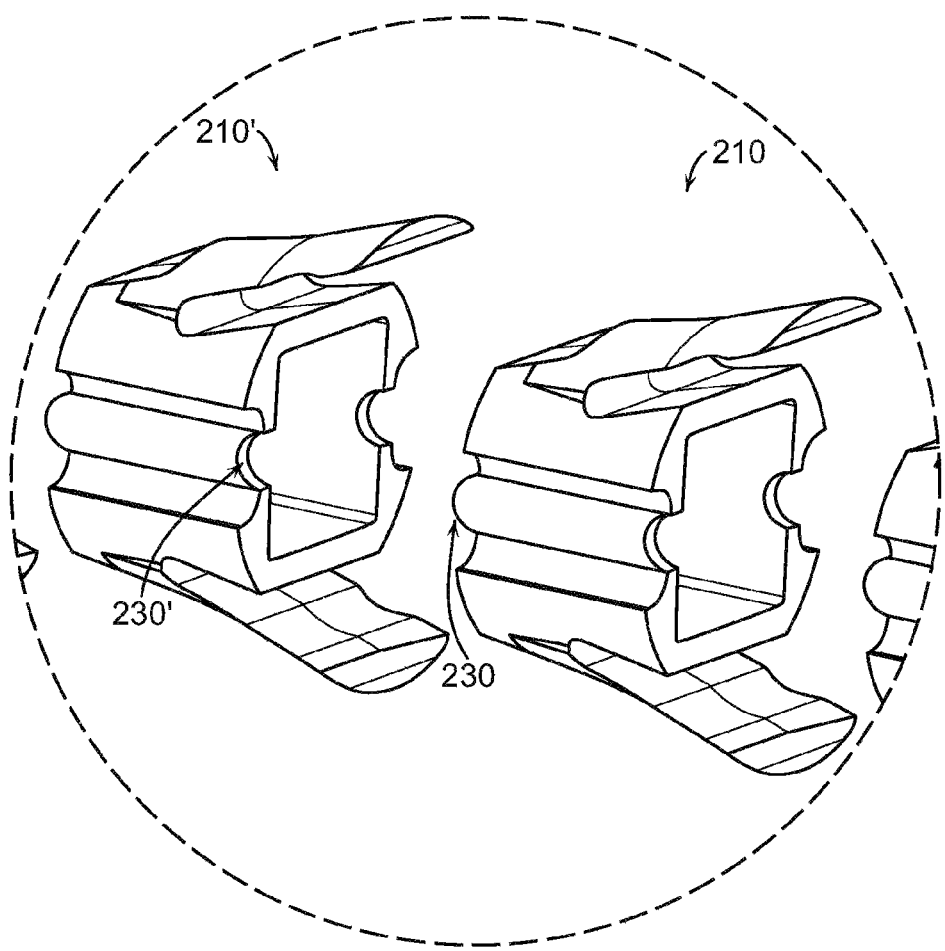

FIG. 5A shows an example of a modular hybrid anchor 200 in which a wing assembly is made up of smaller units called "winglets" 210. Each winglet 210 includes wings (two as shown) and a sleeve similar to those found on the wing assembly 110 described above with reference to FIG. 4. Each winglet 210 further includes one or more alignment features to aid in assembling the hybrid anchor 100. For example, with reference to FIG. 5B, a winglet 210 includes an alignment feature 230 that matches or mates with a corresponding alignment feature 230' of an adjacent winglet 210'. The shape of the alignment feature 230, 230' is semicircular as shown but could be any other suitable shape.

The modular hybrid anchor 200 is assembled, either during the manufacturing process or in the operating room, by fitting (e.g., sliding) the winglets 210 onto a free end 226 of an elongated member 125 of a core body. The assembly is completed by fitting (e.g., snapping or threading) a force receiving member 215 onto the free end 226 of the elongated member 225 of the core body.

The modular design of winglets 210 provides versatility in anchor design. For example, each winglet 210 can be made of different material, each winglet 210 can be individually shaped (e.g., angle of the wings, length of the wings, size of clearance), and/or each winglet 210 can be differently oriented around the longitudinal axis of the core body so that the modular hybrid anchor 200 can achieve a variety of clinical needs.

Some examples of the hybrid anchor 100, 200 include openings formed in the wing assembly 110 or include gaps between the winglets 210. The openings or gaps allow bone to grow into them. This boney ingrowth is desirable and beneficial because it leads to quicker and healthier healing.

Example systems include an inserter with the hybrid anchor 100, 200 described above. The inserter includes a handle and shaft connected to the handle. The shaft includes a distal end. In some examples, the hybrid anchor 100, 200 is located at the distal end of the inserter such that the force receiving member engages the distal end of the inserter. These "preloaded" examples are particular timesaving because a surgeon can install the hybrid anchor 100, 200 without having to take the time to assemble one together. The inserter may include additional features that may be needed to engage and/or to properly install the hybrid anchor 100, 200 (e.g., keyed for one-way insertion, depth stop, etc.).

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. A hybrid anchor comprising:
  a core body made of a material selected from the group consisting of biocomposite, bioabsorbable, osteoconductive, and biocompatible non-absorbable, the core body comprising:
    a proximal end, a distal end, and a longitudinal axis extending therethrough;
    an aperture formed near the distal end of the core body and transverse to the longitudinal axis of the core body, the aperture configured to receive a suture;
    a force receiving member disposed at the proximal end of the core body, the force receiving member configured to engage an inserter and to receive an insertion force applied by the inserter to the core body;
    a tip disposed at the distal end of the core body;
    a stop disposed at the proximal end of the core body; and
    an elongated member extending between the stop and the tip along the longitudinal axis of the core body; and
  a wing assembly made of a polymer, the polymer being different and more flexible than the material of the core body, the wing assembly comprising:
    a sleeve comprising a proximal end, a distal end, and a surface extending therebetween, the sleeve fitted around the elongated member of the core body such that a distal-most end of the sleeve engages the tip and a proximal-most end of the sleeve engages the stop, the distal end of the sleeve being proximal to the aperture and the stop resisting proximal movement of the wing assembly along the elongated member; and
    a plurality of wings formed on diametrically opposing sides of the sleeve and extending outwardly from the surface of the sleeve at an angle towards the proximal end of the sleeve.

2. The hybrid anchor of claim 1 wherein the core body is made of carbon fiber reinforced polyether ether ketone (CF PEEK), polylactic acid (PLA), polyglycolic acid (PGA), polymorphous low-grade adenocarcinoma (PLGA) with calcium-based filler, titanium or stainless steel.

3. The hybrid anchor of claim 1 wherein the sleeve made of polyether ether ketone (PEEK) or Acrylonitrile butadiene styrene (ABS).

4. The hybrid anchor of claim 1 wherein the elongated member has a cross-section selected from the group consisting of a circular cross-section, oval cross-section, regular polygonal cross-section, and irregular polygonal cross-section; and wherein the sleeve has an internal geometry that is the inverse of the cross section of the elongated member.

5. The hybrid anchor of claim 1 wherein the sleeve is radially coupled to the core body.

6. The hybrid anchor of claim 1 wherein the sleeve and core body form an interference fit.

7. The hybrid anchor of claim 1 wherein the sleeve and core body form a friction interface.

8. The hybrid anchor of claim 1 wherein the sleeve is overmolded onto the elongated member.

9. The hybrid anchor of claim 1 wherein the sleeve includes openings allowing for bony ingrowth.

10. The hybrid anchor of claim 1 wherein the force receiving member attaches to the elongated member, and the sleeve includes multiple winglets, each winglet comprising:
  a pair of wings formed on diametrically opposing sides of the winglet; and
  alignment features at opposite ends of the winglet to mate with adjacent winglets.

11. The hybrid anchor of claim 10 wherein the force receiving member attaches to the elongated member with a snap-fit or threads.

12. The hybrid anchor of claim 10 wherein adjacent winglets define an opening between the adjacent winglets allowing for bony ingrowth.

13. The hybrid anchor of claim 1 wherein the tip has a geometry configured for inserting into bone without a hole drilled into the bone.

14. The hybrid anchor of claim 1 wherein a length of the sleeve is substantially equal to a length of the elongated member.

15. The hybrid anchor of claim 1 wherein the aperture is substantially U-shaped, an open end of the U-shaped aperture defining a distal-most end of the elongated body.

16. The hybrid anchor of claim 1 wherein the stop is exterior to the sleeve.

17. A system comprising:
  an inserter comprising a handle and shaft connected to the handle, the shaft including a distal end; and
  a hybrid anchor comprising a core body made of a material selected from the group consisting biocompatible, bioabsorbable, osteoconductive, biocomposite and combinations thereof, and a wing assembly made of a polymer, the polymer being different and more flexible than the material of the core body; the core body comprising:
    a proximal end, a distal end, and a longitudinal axis extending therethrough;
    an aperture formed near the distal end of the core body and transverse to the longitudinal axis of the core body, the aperture configured to receive a suture;
    a force receiving member disposed at the proximal end of the core body, the force receiving member configured to engage the distal end of the inserter and to receive an insertion force applied by the inserter to the core body;
    a tip disposed at the distal end of the core body;
    a stop disposed at the proximal end of the core body; and
    an elongated member extending between the stop and the tip along the longitudinal axis of the core body; and
  the wing assembly comprising:
    a sleeve comprising a proximal end, a distal end, and a surface extending therebetween, the sleeve fitted around the elongated member of the core body such that a distal-most end of the sleeve engages the tip and a proximal-most end of the sleeve engages the stop, the distal end of the sleeve being proximal to the aperture and the stop resisting proximal movement of the wing assembly along the elongated member; and
    a plurality of wings formed on diametrically opposing sides of the sleeve and extending outwardly from the surface of the sleeve at an angle towards the proximal end of the sleeve;
    wherein the hybrid anchor is located at the distal end of the inserter such that the force receiving member engages the distal end of the inserter.

18. The system of claim 17 wherein the force receiving member, the tip and the elongated member form a continuous path configured for the insertion of a substantial portion of the inserter traveling from the proximal end to the distal end of the anchor.

19. The system of claim 17 wherein the stop is exterior to the sleeve.

\* \* \* \* \*